United States Patent
Boss et al.

(10) Patent No.: US 11,049,169 B2
(45) Date of Patent: Jun. 29, 2021

(54) SYSTEM, COMPUTER PROGRAM PRODUCT, AND METHOD FOR AUTOMATED GIFT DETERMINATION AND DELIVERY

(71) Applicant: INTERNATIONAL BUSINESS MACHINES CORPORATION, Armonk, NY (US)

(72) Inventors: Gregory J. Boss, Saginaw, MI (US); Bernadette Pierson, South Hero, VT (US); Cesar Augusto Rodriguez Bravo, San Rafael de Alajuela (CR); Jayashree Vaidyanathan, Cincinnati, OH (US)

(73) Assignee: International Business Machines Corporation, Armonk, NY (US)

( * ) Notice: Subject to any disclaimer, the term of this patent is extended or adjusted under 35 U.S.C. 154(b) by 245 days.

(21) Appl. No.: 16/043,601

(22) Filed: Jul. 24, 2018

(65) Prior Publication Data

US 2020/0034914 A1    Jan. 30, 2020

(51) Int. Cl.
| | |
|---|---|
| *G06Q 30/00* | (2012.01) |
| *G06Q 30/06* | (2012.01) |
| *A61B 5/16* | (2006.01) |
| *G06K 9/72* | (2006.01) |
| *G06F 40/30* | (2020.01) |

(52) U.S. Cl.
CPC ......... *G06Q 30/0633* (2013.01); *A61B 5/165* (2013.01); *G06F 40/30* (2020.01); *G06K 9/726* (2013.01); *G06Q 30/0609* (2013.01); *G06Q 30/0631* (2013.01)

(58) Field of Classification Search
CPC . G06Q 30/0633; G06Q 30/0609; G06F 40/30
USPC ..................................................... 705/26.8
See application file for complete search history.

(56) References Cited

U.S. PATENT DOCUMENTS

| | | | |
|---|---|---|---|
| 7,881,971 | B1 | 2/2011 | Nguyen et al. |
| 7,970,657 | B2 | 6/2011 | Morgenstern |
| 8,132,100 | B2 | 3/2012 | Seo et al. |
| 9,231,989 | B2 | 1/2016 | Milliken |
| 2008/0243630 | A1 | 10/2008 | Farney |
| 2010/0082751 | A1* | 4/2010 | Meijer .................... G06F 15/16 709/206 |

(Continued)

OTHER PUBLICATIONS

O'Banion, S. (2014). Using explicit expressions of preference and choice in social media for prediction and recommendation (Order No. 3626982). Available from ProQuest Dissertations & Theses Global. (1559092075). (Year: 2014).*

(Continued)

*Primary Examiner* — Jason B Dunham
*Assistant Examiner* — Arielle E Weiner
(74) *Attorney, Agent, or Firm* — Schmeiser, Olsen & Watt; Nicholas L. Cadmus

(57) ABSTRACT

A system and method for automated gift determination and delivery is provided, which include identifying a contact from an electronic contact list for receiving a gift, detecting from first data related to the contact a change in an emotional state of the contact, validating from second data the change in the emotional state of the contact, and automatically selecting the gift from a plurality of identified gifts that is determined to be commensurate with the change status and a current emotional state of the contact.

18 Claims, 7 Drawing Sheets

(56) References Cited

U.S. PATENT DOCUMENTS

| | | | |
|---|---|---|---|
| 2013/0245396 A1* | 9/2013 | Berman | G06F 19/3418 |
| | | | 600/301 |
| 2014/0025620 A1* | 1/2014 | Greenzeiger | G06Q 30/02 |
| | | | 706/47 |
| 2014/0089131 A1 | 3/2014 | Batra et al. | |
| 2014/0316937 A1 | 10/2014 | Jiao et al. | |
| 2016/0171110 A1* | 6/2016 | Gao | H04L 67/306 |
| | | | 707/734 |
| 2017/0098197 A1* | 4/2017 | Yu | G06Q 30/02 |
| 2020/0279156 A1* | 9/2020 | Cai | G06N 3/04 |

OTHER PUBLICATIONS

Nomura, Miki; Gift Giving Anxieties as a Function of Recipient Characteristics; The Graduate Schol, University of Wisconsin-Stout; May 2009; 67 pages.

Nomura, Miki; Gift Giving Characteristics of Recipients and Function of Fiting Anxieties; Graduate Student, Applied Psychology; University of Wisconsin; 2009; 24 pages.

Anonymous; Social Data Analysis as unobtrusive measure for validating human behavior assessment or test (Psychometric) results; IP.com; IPCOM000208050D; Jun. 21, 2011; 10 pages.

Mayet, C. et al.; The Psychology of Gift Exchange; University of Hertfordshire; Internal Report 2010; 9 pages.

Anonymous; Cognitive Personal Shopping Assistant Optimized on Shopper's Profile; IP.com; IPCOM000241828D; Jun. 2, 2015; 6 pages.

* cited by examiner

SYSTEM, COMPUTER PROGRAM PRODUCT, AND METHOD FOR AUTOMATED GIFT DETERMINATION AND DELIVERY

BACKGROUND

The present invention relates to gift giving, and more specifically to gift giving based on the detection and analysis of an emotional state of a potential recipient of the gift.

It is well-known for people to be sensitive to another person's emotional state. When two people have a relationship, for example, friends or family members, and one of the people is sad or upset, it is often desirable for the other person to send flowers or other gifts to the unhappy person.

SUMMARY

An embodiment of the present invention relates to a method, and associated computer system and computer program product, for automated gift determination and delivery. A processor of a computer system identifies a contact from an electronic contact list for receiving a gift, detects from first data related to the contact a change in an emotional state of the contact, validates from second data the change in the emotional state of the contact; and automatically selects the gift from a plurality of identified gifts that is determined to be commensurate with the change in the emotional state and a current emotional state of the contact.

DETAILED DESCRIPTION

Figure 1:
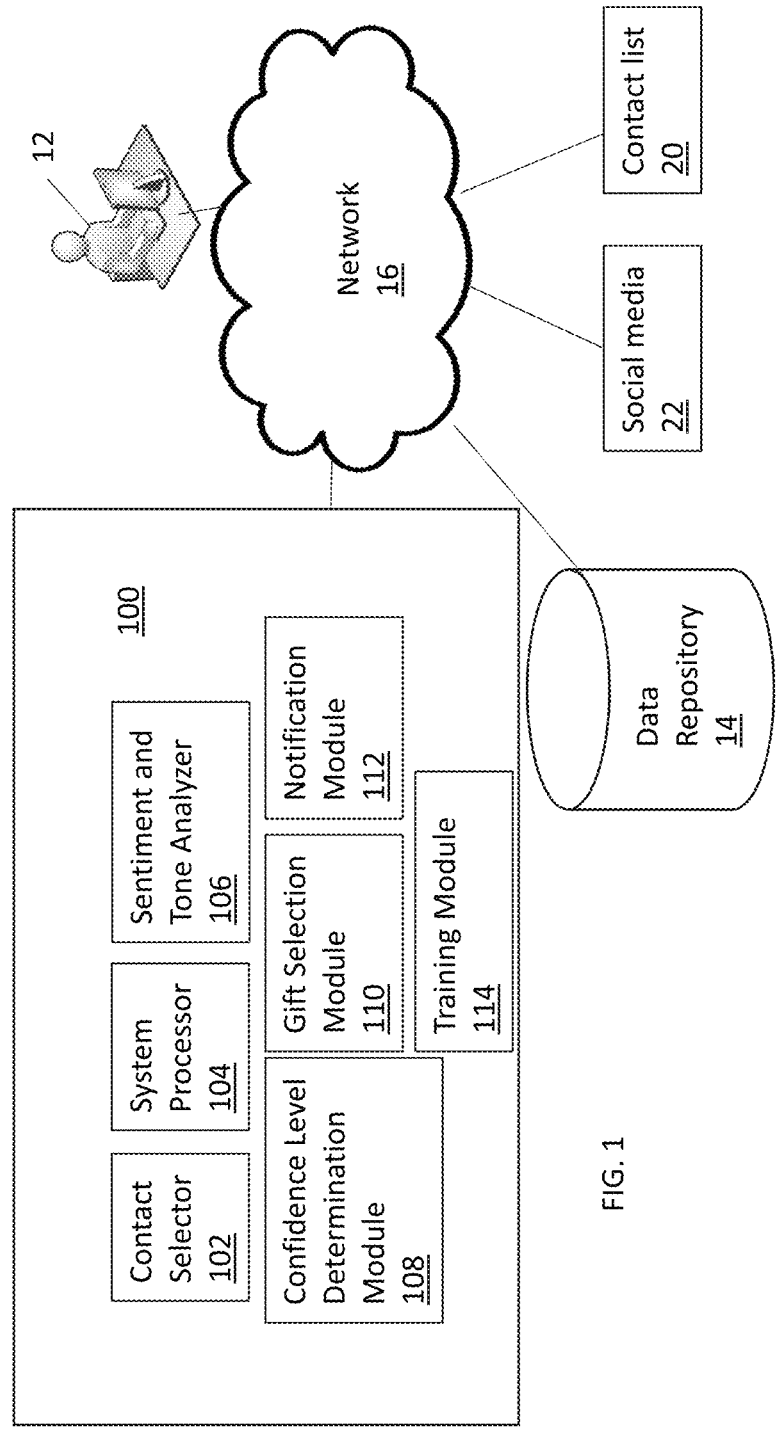
FIG. 1 depicts a block diagram of a gift selection and delivery system, in accordance with embodiments of the present invention.

In brief overview, provided in some embodiments are a system and method for quickly and appropriately reacting to a change in emotional state of a contact, especially in cases where one person is at a remote location from a friend, family member, acquaintance, or other contact who experiences a change in an emotional state unbeknownst to the remote person but determined from data received by computer-based information sources and processed and analyzed to determine a particular gift commensurate with the emotional state of the identified contact. Some embodiments of the inventive concept provide a solution that provides automatic gift giving in situations where one person has not responded to another person such as a friend or family member who is a candidate for receiving a gift based on a detection and analysis of a change in emotional state of the other person. In some embodiments, the system and method determines when someone may be in need of encouragement, solace, or reassurance based on a substantial change in emotional state. In some embodiments, the system and method associates a confidence level to a reason for the change in emotional state. In some embodiments, the system and method allows the user to pre-approve a gift, gift recipient, consoling message, and/or other information in advance of providing the gift according to the intended recipient's emotional state. In some embodiments, a user pre-selects contacts who are eligible for possible gifts according to an automated gift system. This may include specific parameters, such as the maximum gift cost, frequency at which automated gift-giving may be performed, and so on.

In some embodiments, a gift, gift recipient, and/or gift message can be pre-approved, or otherwise selected, with a single action performed by a computer mouse, stylus, or the like that reduces the number or interactions needed to pre-approve a gift automatically identified by a gift selection and delivery system for a selected recipient determined according to data collected that is processed to establish a state of mind and/or emotional status change of the selected recipient.

For example, an email message may be generated and output to a user that includes a uniform resource locator (URL) that corresponds to an internet address or the like that receives a user's approval to provide a gift under predetermined conditions when the user selects the URL from a display. Here, a URL may be generated by the system in response to a determination of the emotional status change, a confirmation of a confidence level of the status change, and an identification of potential gifts, so that the user does not need to undergo the time-consuming steps of learning about the emotional state change and laborious gift-searching exercise. In another example, a pop-up notification may be displayed at the user's smartphone with a display button for approving a gift selection, e.g., using a mouse or touchscreen to select the button. In another example, a text message may be displayed on the user's smartphone requesting that the user approve a gift selection. In another example, a voice recording or computer-generated audio message from a computer device such as Google Home™ or Amazon Alexa™ may be output asking that the user provide a voice response regarding the approval of a gift selection. In another example, a telephone keypad from a smartphone or conventional telephone may be used to respond to an audio message, i.e., dual-tone multi-frequency (DTMF) signaling, from an automated phone call request approval of a gift selection. The concepts herein are not limited to these examples.

In some embodiments, the system and method provides a computing environment to quickly and accurately react to situations where a person may not learn of a change in emotional status of a friend, family member, coworker, and so on, but automatically reduces the time it takes to identify an appropriate gift and deliver it to that other person, for example, by providing a single-click feature for electronically performing this task, and to train the computer system to learn from previous events involving this gift recipient, from example, who may be prone to hyperbole-related emotions, and improve the accuracy of future determinations by an artificial intelligence system with respect to whether to send a gift under similar circumstances, whether to send a particular gift and/or message associated with the gift, and so on.

Referring to the drawings, FIG. 1 depicts a block diagram of a gift selection and delivery system 100 as part of an overall system, in accordance with embodiments of the present invention. The gift selection and delivery system 100 is constructed and arranged to assess the emotional states of people or groups of people who may be candidates for receiving a gift initiated by a friend, family member, or other gift-giving person. The system 100 also provides for the ability for a user to pre-select contacts from a stored listing of contacts for receipt of a selected gift, which is automatically delivered to the contact according to an assessed emotional state and/or other established criteria. In addition to the gift selection and delivery system 100, the overall system 10 may include a program executed at a user computer 12, a data repository 14, and various communication interfaces to third party computers, for example, described with reference to embodiments herein.

The gift selection and delivery system 100 includes a contact selector 102, a system processor 104, a sentiment and tone analyzer 106, a confidence level determination module 108, a gift selection module 110, a notification module 112, and a training module 114. Some or all of these elements of the system may be part of a same hardware computer platform for example, executed by a common processor, or may be physically separate from each other, i.e., stored and executed by physically disparate hardware computer platforms, and in communication with each other via a data communication network 16, e.g., a local area network (LAN) or a wide area network (WAN). In some embodiments, the gift selection and delivery system 100 includes a memory device or related computer readable storage device is coupled to one or more of the contact selector 102, system processor 104, sentiment and tone analyzer 106, confidence level determination module 108, gift selection module 110, and notification module 112. The storage device contains program code executable by the processor via the memory device to implement a method for automated gift determination and delivery, for example, method 200 of FIG. 2 or method 300 of FIG. 3.

The contact selector 102 includes an input for receiving data regarding a selection of a contact. For example, a user can identify one or more contacts as potential recipients of a pre-approved gift. In some embodiments, a user can select on a user interface of a computer 12 a contact from the user's electronic contact list 20, social listing of friends, profile or other data source that includes information about the user's friends, family members, business acquaintances, social circles, and so on. In some embodiments, the contact selector 102 can be preprogrammed so that one or more contacts in a particular grouping can be identified as automatic recipients of gifts. In some embodiments, the contact selector 102 incorporates or otherwise executes an application plugin, application programming interface (API), or other computer interface that establishes a data communication with an online social network computer website to retrieve data regarding potential gift recipients identified in the social network listing, and/or social media postings on the website, electronic communications such as email messages, text messages, and so on.

Figure 4:
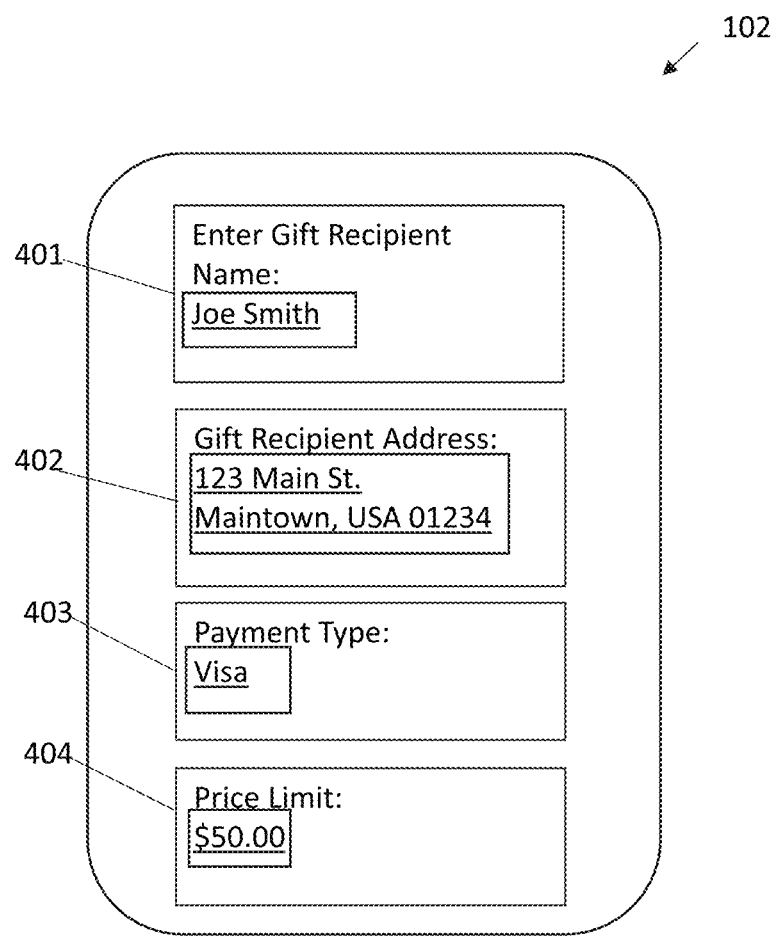
FIG. 4 depicts a screenshot of a user interface that permits a user to select a gift for an intended recipient, in accordance with embodiments of the present invention.

During operation, as shown in FIG. 4, the user can enter or otherwise select the name or identifier (401) of a potential recipient of a gift from the electronic contact list 20. In response to the selection, the name of other identifier of the potential gift recipient is stored by the contact selector 102 locally or at the data repository 14. In some embodiments, the social network contact list 20 is collocated with emotional state data corresponding to potential gift recipients of the contact list 20 at the data repository 14.

The system processor 104 is configured to process received data regarding potential recipients selected from the contact list 20 as candidates for receiving gifts and facilitates the exchange of the processed data with the other components of the gift selection and delivery system 100. For example, the system processor 104 can associate a potential gift recipient selected from the contact list 20 and corresponding information such as address, interests, family status, recently posted electronic messages on a social website, and so on with other relevant data, such as an e-commerce website where flowers, candy, or other gifts may be purchased. In some embodiments, the system processor 104 can generate a table, matrix, or the like that associates specific contacts with specific gifts, and further associates specific gifts with specific emotional states of a contact. For example, the system processor 104 may collect data that establishes that a particular potential gift recipient selected from the contact list 20 is the best friend of the user, and that this person enjoys a particular brand of chocolate candy. The system processor 104 can prepare a table that establishes this correlation.

The sentiment and tone analyzer 106 is configured to analyze the user's electronic contact list 20, or more specifically, social media posts, text messages, or other data of potential gift recipients of the contact list 20. Although a contact list 20 is shown in FIG. 1 as being in communication with the user computer 12 via a network 16, in some embodiments, the contact list 20 is electronically stored and executed at the user computer 12. The sentiment and tone analyzer 106 can determine from this collected data a previous and/or current emotional state of a selected possible gift recipient and/or a change in emotional state of the selected possible gift recipient. Historical emotional state data can be compiled and stored at the data repository 14 for subsequent retrieval to determine confidence levels of emotional state changes, reasons for emotional state changes, and so on. In some embodiments, the sentiment and tone analyzer 106 can modify a registered emotional status in response to determined context data, changes in the emotional status, time delays, and so on.

In some embodiments, the sentiment and tone analyzer 106 includes a cognitive analyzer that includes an artificial intelligence system or is part of an artificial intelligence system that is capable of answering questions in the natural language and simulates of human thought processes in a computer model. The cognitive analyzer can execute a process, which can incorporate artificial intelligence technology to answer questions posed using a natural language and enabling definition of complex data analytics based on a corpus in which patterns and trends are setup and generated and can interact with a proposed solution. For example, the system may discern that a particular contact is sad because she lost her father. In doing so, the sentiment and tone analyzer 106 may collect and analyze historical decisions made by the system for training the computer system, for example, the artificial intelligence features of the system, to improve its accuracy for future decisions provided by the training module 114, which processes a result of the sentiment and tone analyzer 106 for input to a knowledge base, data repository, machine learning, neural network, and/or artificial intelligence computer, for example, part of one or more elements of the computing architecture as shown in FIG. 1 in order to train such computer elements by a direct output with respect to future decisions on gift determinations for identified recipients. For example, multiple iterations may be processed where for each iteration a specific gift is identified and the contextual data contributing to the decision to select the specific gift is stored at a database or the like and subsequently retrieved and output to the machine learning system for a next gift determination process.

The confidence level determination module 108 is configured to calculate a confidence level of the reason for a status change in a potential gift recipient's emotional state. For example, the confidence level determination module 108 may discern that a potential gift recipient is sad due to the death of her pet dog. In other embodiments, a reason for a potential gift recipient's emotional state, or the status of the change in emotional state, may not be determined due to a lack of information, whereby the confidence level determination module 108 calculates a probability of the confidence level on the reason for a status change in a potential gift recipient's emotional state without this information. In some embodiments, the confidence level determination module 108 includes a cognitive analyzer that provides artificial intelligence to determine from the collected data whether the contact has a tendency for hyperbolic emotions, whereby the system may determine not to send a gift but instead store this information to train the computer system to improve its accuracy for future decisions. An iteration process extending between these electronic elements of the system can improve a result calculated by the machine learning, neural network, and/or artificial intelligence computer, thereby training, updating, and optimizing the system to efficiently identify relevant gifts according to a high degree of accuracy with respect to the determined state of mind of the recipient.

The gift selection module 110 is configured to automatically identify a gift for a selected contact in response to a determination that a calculated confidence level is greater than a threshold value. As described above, a table, matrix, or the like may be generated and stored at the data repository 14 that identifies gifts associated with a particular contact. When the system determines an acceptable confidence level of a reason for a change in emotional state of the change, the gift selection module 110 can identify a gift from a listing of gifts or from the table, matrix, or the like that is commensurate with the type of emotional state, for example, happy, sad, angry, and so on. In some embodiments, a contact may not have a gift associated with the emotional state, or identified as a possible recipient of a gift. Here, the gift selection module 110 can receive and process data regarding other contacts and their gifts, and a gift may be identified from an analysis of this other data. For example, the gift selection module 110 may establish that the majority of people in a contact list are identified as receiving candy, clothing, sporting event tickets, and so on when it is determined that they are depressed. When a new contact is added to the list and is determined to be a male adult, this new contact can automatically be identified as receiving a baseball game tickets when he is depressed.

The notification module 112 is configured to generate and output a notification the user of the delivery of the gift and/or other information that is relevant to the gift delivery. For example, an email message can be provided to the user's computer 12 of an automatic delivery of a gift to a contact determined to be distraught over the death of a family member.

Figure 2:
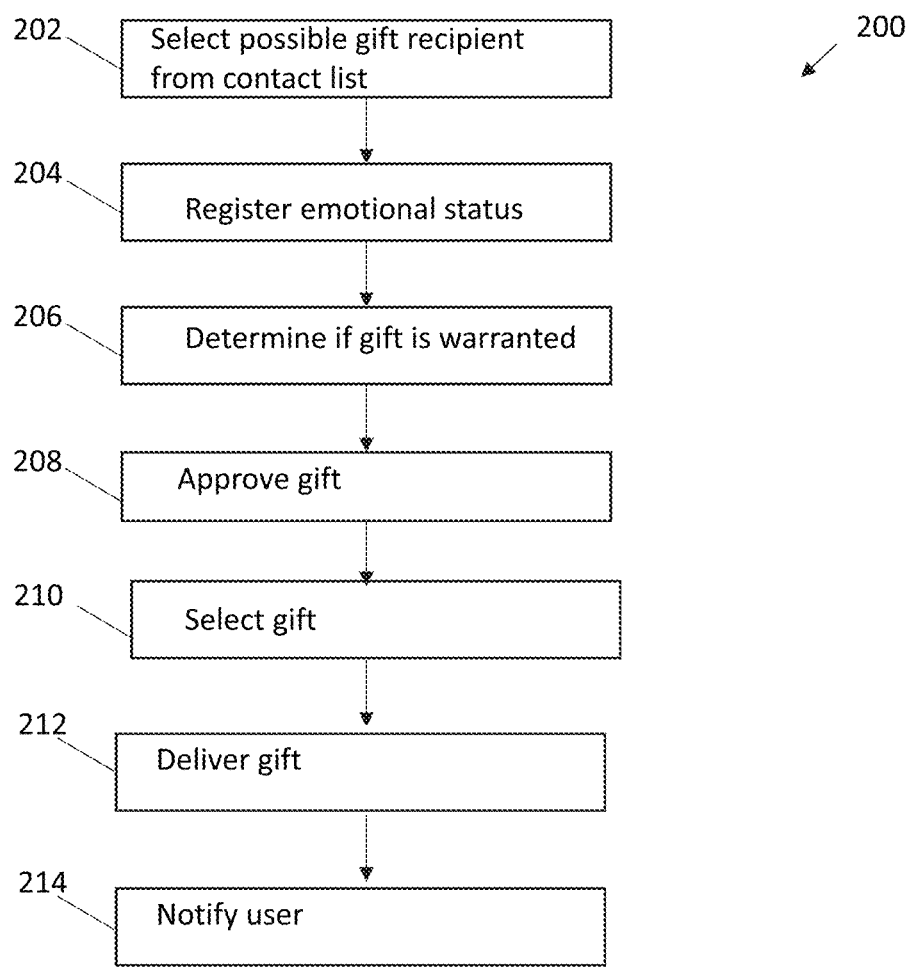
FIG. 2 depicts a flow chart of a method for automated gift delivery, in accordance with embodiments of the present invention.

FIG. 2 depicts a flow chart of a method 200 for automated gift delivery, in accordance with embodiments of the present invention. One embodiment of the method 200 or algorithm that may be implemented by incorporating some or all of the computing elements of the system described in FIG. 1, one or more computer systems as defined generically in FIG. 5.

At block 202, a computer user selects on a user interface 102 of a mobile device, tablet, personal computer, or other computing device an identification of one or more people of interest who may be possible recipients of a gift provided by the user. The identification may be determined from personal contacts such as friends or family members listed in the user's electronic contact list 20, or social network profile or other data source that stores contact information. The contacts are selected for possibly receiving future gifts. For example, referring again to FIG. 4, selected contacts (401) allow the system processor 104 to identify the contact as well as other information such as an address (402) of the contact to send a gift. In setting this up, the user can also set up a payment method (403), such as credit card information for automatically purchasing a gift when a contact is selected for actually receiving a gift. Other information such as a price limit (404) may be entered.

At block 204, an emotional state of a selected possible gift recipient is determined by the sentiment and tone analyzer 106 and registered by the system processor 104 at the data repository 14. The sentiment and tone analyzer 106 can access a social media website or the like to access information for analysis about an emotional state of a potential gift recipient of the contact list 20. For example, the sentiment and tone analyzer 106 can determine from a recent message posted to a potential gift recipient's social media account 22 that the potential gift recipient announced her wedding engagement to a longtime boyfriend.

The sentiment and tone analyzer 106 can determine that the emotional state of the potential gift recipient is happy, ecstatic, and so on. The analyzer 106 can parse keywords from the message such as the name of the boyfriend, the date of the wedding proposal, and so on. This data can be used to identify an appropriate gift. In some embodiments, the keywords can be automatically inserted into a predetermined boilerplate language added to a card to be sent with the gift. The emotional state details may be stored at the data repository 14 for subsequent retrieval and use when determining confidence levels, a change in the emotional status, and so on.

In some embodiments, the sentiment and tone analyzer 106 can modify a registered emotional status in response to determined context data, changes in the emotional status, factors such as time delays, and so on. For example, a contact may be determined to be depressed for one month, where a context analyzer of the sentiment and tone analyzer 106 provides a determination in response to received context data that this contact should not receive a gift every day, whether the contact should receive an expensive gift, or whether a predetermined user-provided parameter is to be modified or bypassed if determined context data exceeds a threshold. In another example, the emotional status of a contact may change every week, where a determination is made that this contact should not receive a gift every week, but instead change the parameters so that the contact receives a gift once a month. In another example, a contact may have recently lost her job one week followed by the death of a parent the next week. Here, a gift is warranted for each of these events.

At block 206, a determination is made whether a gift is warranted for the selected possible gift recipient in response to a determination and registration of the change in emotional state. For example, a potential gift recipient who is given to hyperbole may not receive any gift, regardless of emotional status. For example, historical data stored at the data repository 14 may reveal that a potential gift recipient tends to exaggerate his emotions, for example, posting messages exhibiting exhilarant behavior for trivial events. This determination can be made by comparing a current posting at the social media website 22 with previous postings and applying the analyzer 106 to determine trends, changes in patterns with respect to the tone of the social media postings, and so on.

At block 208, the gift is approved for purchase and delivery to and receipt by the selected gift recipient. In some embodiments, the gift is automatically approved, with no user interaction. In other embodiments, user interaction is required, for example, selecting a URL in a received email message, a button in a pop-up notification or a text message on the user's mobile device, a voice notification from a computer-generated voice request, and so on.

At block 210, the gift is selected according to the determined emotional state of the gift recipient. In some embodiments, the gift is selected according to a table, matrix, or the like that identifies specific gifts with specific emotional states of the gift recipient, for example, flowers selected for sadness, candy for love, and so on. Other approaches for selecting a gift may equally apply. In other embodiments, the system may electronically track a recipient's social media 22 to acquire data about the recipient's hobbies, and identify potential gifts based on this acquired data. For example, a contact's social media postings may suggest that the contact enjoys fine wine and sailing, where a gift may be selected that includes a particular brand of wine and/or a book on sailing. In other embodiments, the system may collect historical data on a user's gifts to establish the effectiveness of certain gifts with respect to changing an emotional state. For example, the sentiment and tone analyzer 106 may access the data repository 14 to collect data that establishes that a particular brand of chocolate went previously delivered to a contact resulted in a positive change in the contact's emotional state.

At block 212, the selected gift is delivered to the selected gift recipient. In some embodiments, the selected gift can be automatically purchased via an e-commerce communication between the gift selection and delivery system 100 and a website or other online location where the gift can be purchased. Purchase data such as credit card information and so on can be retrieved from user information stored at the data repository 14.

At block 214, the user receives a notification, for example, an email message or text message, that is generated by the notification module 112 of the gift selection and delivery system 100 after the gift has been purchased and/or delivered. In some embodiments, a prerecorded typed, audio, and/or video message is stored at the data repository 14 and automatically retrieved by the notification module 112 for processing and output to a personal computer 12 of the user.

Figure 3:
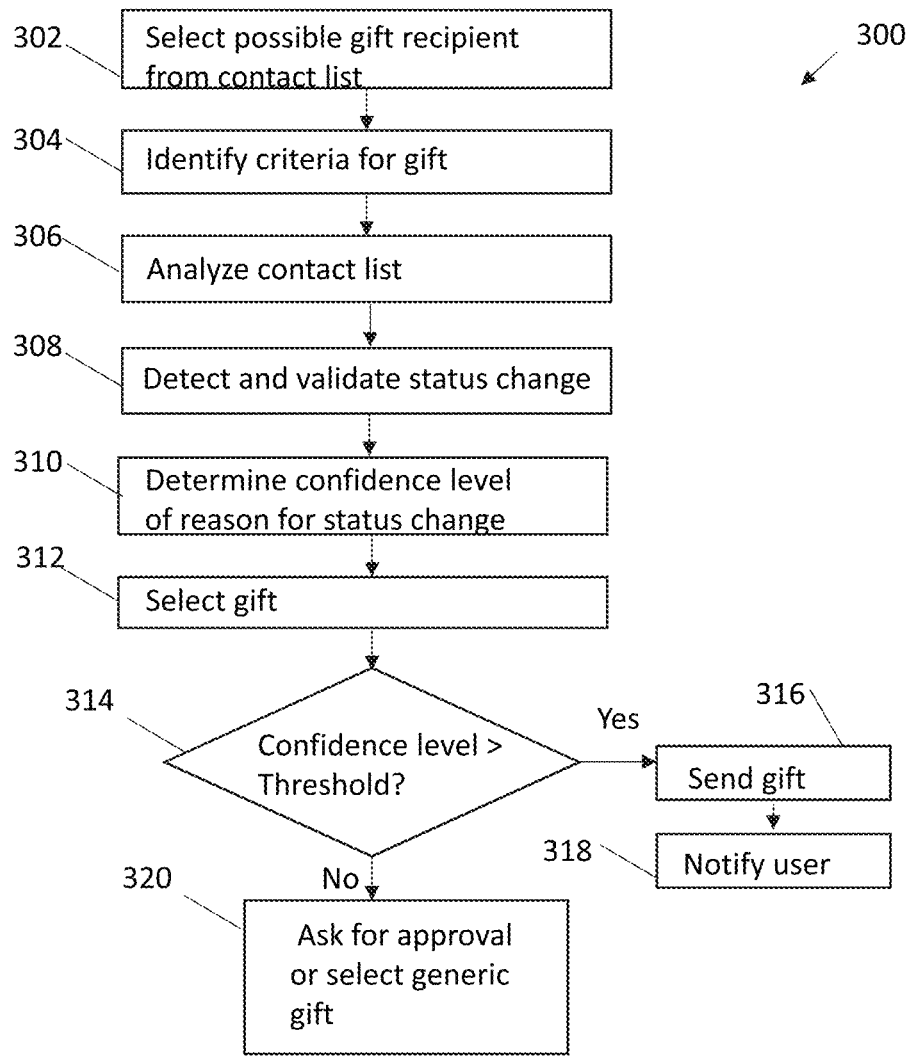
FIG. 3 depicts a flow chart of a method for configuring a special-purpose computer to select a gift according to an intended recipient's emotional state, in accordance with embodiments of the present invention.

FIG. 3 depicts a flow chart of a method 300 for configuring a special-purpose computer to associate a confidence level to a reason for a change in emotional state, in accordance with some embodiments. One embodiment of the method 300 or algorithm that may be implemented by incorporating some or all of the computing elements of the system described in FIG. 1, one or more computer systems as defined generically in FIG. 5.

At block 302, a computer user selects on a user interface 102 of a mobile device, tablet, personal computer, or other computing device an identification of one or more people of interest who may be possible recipients of a gift provided by the user. The identification may be determined from personal contacts such as friends or family members listed in the user's electronic contact list 20, or social network profile or other data source that stores contact information. The contacts are selected for possibly receiving future gifts. Selected contacts allow the system processor 104 to identify the contact as well as other information such as an address of the contact to send a gift. In setting this up, the user can also set up a payment method, such as credit card information for automatically purchasing a gift when a contact is selected for actually receiving a gift.

At block 304, the user can enter into the computer display a set of gift criteria. For example, the user can enter a price limit on a gift, or a type of gift, or a particular gift for a selected contact. In some embodiments, names or other information of one or more gifts may be selected for a particular contact of interest to the user.

At block 306, the user's electronic contact list, or more specifically, social media posts, text messages, or other accessible information displayed electronically on network-connected computers by the user's contacts is analyzed by the sentiment and tone analyzer 106 to ascertain individuals and identify data related to identified contacts, derive personality and behavioral traits, and so on.

At block 308, a status change in one or more contacts is detected and validated. In some embodiments, the change in emotional state is determined by comparing prior social media posts made by the person of interest. For example, a derived profound or drastic change in emotional state in block 306 can be determined from a comparison of a current social media post that a selected contact had a death in the family to a previous post from the same contact that the contact had a pleasant day.

At block 310, at least one of a probable cause and a confidence level of the reason for status change are calculated. The probable cause or likely reason for the status change is determined from data analyzed by the confidence level determination module 108, for example, data collected about a past relationship status, posts, pictures, and so on of a relationship, a change in a user's profile from "in a relationship" to "single," and other indications of a breakup in the relationship. The confidence level of the reason for the status change is determined by the same or similar data. However, additional data such as historical information may be processed, for example, by the analyzer 106 and/or confidence level determination module 108, to establish the confidence level for the reason for a change in a particular emotional state. Referring to the previous example, the confidence level determination module 108 may calculate a 100% confidence level that a breakup occurred. Thus, embodiments provide for a confidence level that can be associated with an emotional state.

At block 312, the system selects a gift that is determined by the system that the selected contact would appreciate. In some embodiments, the system determines the gift based on the contact profile and social media postings in addition to a reason for the change in emotional state. In other embodiments, the system relies on preconfigured options to determine the gift.

At decision diamond 314, a determination is made by the confidence level determination module 108 whether the confidence level is within a pre-defined threshold, for example, 97%. The threshold value is stored in a computer memory and accessed by the confidence level determination module 108 when performing the comparison. The threshold value may be preconfigured at the factory, or configured by a user, for example, changed to a different value. If yes, then at block 316 the system generates and outputs a data signal to the gift selection module 110 and/or notification module 112, which automatically notifies a source of the gift, for example, a retail store, flower shop, and so on, which may have a delivery service or otherwise send in response to a request to a delivery service to deliver the gift selected at block 312 to the intended recipient. In some embodiments, a message can be automatically generated to be provided to the recipient with the gift. For example, in the previous example where a breakup is determined with a high degree of confidence, a bouquet of flowers can be automatically selected along with a note that includes a predetermined message, for example, "Today was a bad today but tomorrow will be better." Predetermined messages can be recorded and stored at the data repository 14, or other database remote from but in communication with the system.

If no, then the method proceeds to block 320, where different actions or no action may be taken. In some embodiments, the system generates a status that is output to the user as a notification, for example, a previous status, a current status, details on a selected gift, or a combination thereof, then requests that the message recipient approve the receipt of the gift. The user may approve the gift by selecting a button, icon, or the like displayed on the user's computer 12. In other embodiments, a generic gift such a flower bouquet or a greeting card may be selected along with a message, which may or may not require user approval.

In some embodiments, the content of the message generated by the notification module 112 varies depending on the confidence level value generated by the confidence level determination module 108. For example, a determination may be made that a user's contact may have recently lost a parent based on the collected social media posts and/or other data. The system may generate a first message for delivery with a gift if the confidence level is greater than the threshold but less than 100% confidence, for example, "You are in our prayers." However, The system may generate a second message if the confidence level is 100%, for example, "Sorry for your loss." In this example, the 100% confidence level may be established by an analysis of a combination of recent media postings stating "It has been a rough day. Dad went on life support" and "Dad has taken a turn for the worse" combined with a current posting that states "RIP Dad."

In another example, a determination made be made that a contact recently started a new job. Here, the system may generate a first message for delivery with a gift if the confidence level is greater than the threshold but less than 100% confidence, for example, "I am so happy for you." However, the system may generate a second message if the confidence level is 100%, for example, "Congratulations on your new job." In these examples, the confidence level is determined from collected social media posts and/or other data that establishes the degree of confidence, whereby the message is determined by the confidence level.

Figure 5:
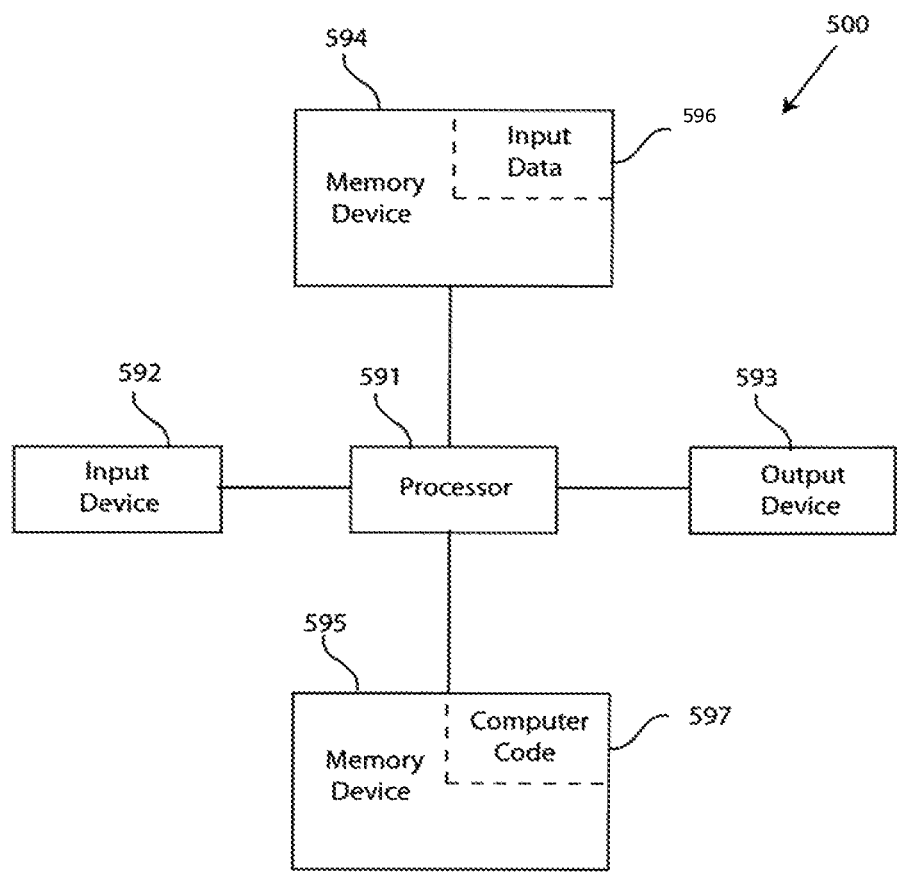
FIG. 5 illustrates a block diagram of a computer system capable of implementing a cognitive service in an IoT environment, in accordance with embodiments of the present invention.

FIG. 5 illustrates a block diagram of a computer system 500 that may be included in the system of FIG. 1 and the methods illustrated in FIGS. 2 and 3 in accordance with the embodiments of the present disclosure. The computer system 500 may generally comprise a processor 591, an input device 592 coupled to the processor 591, an output device 593 coupled to the processor 591, and memory devices 594 and 595 each coupled to the processor 591. The input device 592, output device 593 and memory devices 594, 595 may each be coupled to the processor 591 via a bus. Processor 591 may perform computations and control the functions of computer 500, including executing instructions included in the computer code 597 for the tools and programs capable of implementing a method, in the manner prescribed by one or more elements of the system and methods described with respect to FIGS. 1-4, wherein the instructions of the computer code 597 may be executed by processor 591 via memory device 595. The computer code 597 may include software or program instructions that may implement one or more algorithms for implementing the methods of providing a result, as described in detail above. The processor 591 executes the computer code 597. Processor 591 may include a single processing unit, or may be distributed across one or more processing units in one or more locations (e.g., on a client and server).

The memory device 594 may include input data 596. The input data 596 includes any inputs required by the computer code 597. The output device 593 displays output from the computer code 597. Either or both memory devices 594 and 595 may be used as a computer usable storage medium (or program storage device) having a computer readable program embodied therein and/or having other data stored therein, wherein the computer readable program comprises the computer code 597. Generally, a computer program product (or, alternatively, an article of manufacture) of the computer system 500 may comprise said computer usable storage medium (or said program storage device).

Memory devices 594, 595 include any computer readable storage medium, including those described in detail below. In one embodiment, cache memory elements of memory devices 594, 595 may provide temporary storage of at least some program code (e.g., computer code 597) in order to reduce the number of times code must be retrieved from bulk storage while instructions of the computer code 597 are executed. Moreover, similar to processor 591, memory devices 594, 595 may reside at a single physical location, including one or more types of data storage, or be distributed across a plurality of physical systems in various forms. Further, memory devices 594, 595 can include data distributed across, for example, a local area network (LAN) or a wide area network (WAN). Further, memory devices 594, 595 may include an operating system (not shown) and may include other systems not shown in FIG. 6.

In some embodiments, the computer system 500 may further be coupled to an Input/output (I/O) interface and a computer data storage unit. An IVO interface may include any system for exchanging information to or from an input device 592 or output device 593. The input device 592 may be, inter alia, a keyboard, a mouse, etc. or in some embodiments the sensors 110. The output device 593 may be, inter alia, a printer, a plotter, a display device (such as a computer screen), a magnetic tape, a removable hard disk, a floppy disk, etc. The memory devices 594 and 595 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus may provide a communication link between each of the components in computer 500, and may include any type of transmission link, including electrical, optical, wireless, etc.

An IVO interface may allow computer system 500 to store information (e.g., data or program instructions such as program code 597) on and retrieve the information from computer data storage unit (not shown). Computer data storage unit includes a computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk). In other embodiments, the data storage unit may include a knowledge base or data repository, for example, part of one or more elements of the computing architecture as shown in FIG. 1.

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider that offers to deploy or integrate computing infrastructure with respect to cognitive computer systems and methods. Thus, an embodiment of the present invention discloses a process for supporting computer infrastructure, where the process includes providing at least one support service for at least one of integrating, hosting, maintaining and deploying computer-readable code (e.g., program code 597) in a computer system (e.g., computer 500) including one or more processor(s) 591, wherein the processor(s) carry out instructions contained in the computer code 597 Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements a method of automated gift determination, gift selection according to an intended recipient's emotional state, and so on. Thus, the present invention discloses a process for supporting, deploying and/or integrating computer infrastructure, integrating, hosting, maintaining, and deploying computer-readable code into the computer system 500, wherein the code in combination with the computer system 500 is capable of performing a method for providing an availability recommendation.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
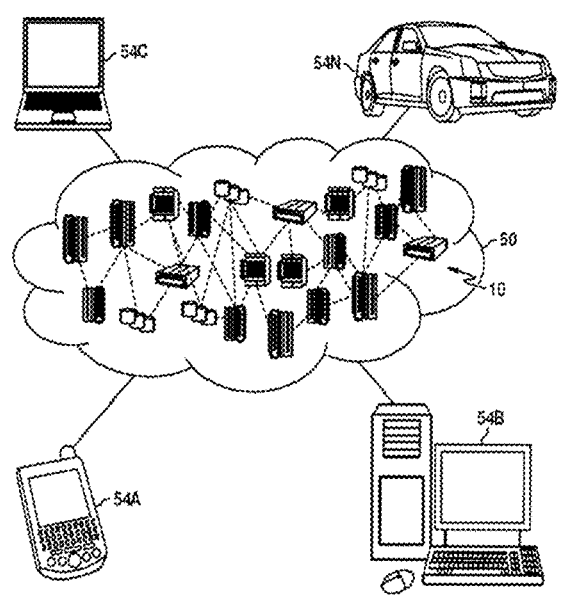
FIG. 6 depicts a cloud computing environment, in accordance with embodiments of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 6 are intended to be illustrative only and that computing nodes 10 and cloud computing environment 50 can communicate with any type of computerized device over any type of network and/or network addressable connection (e.g., using a web browser).

Figure 7:
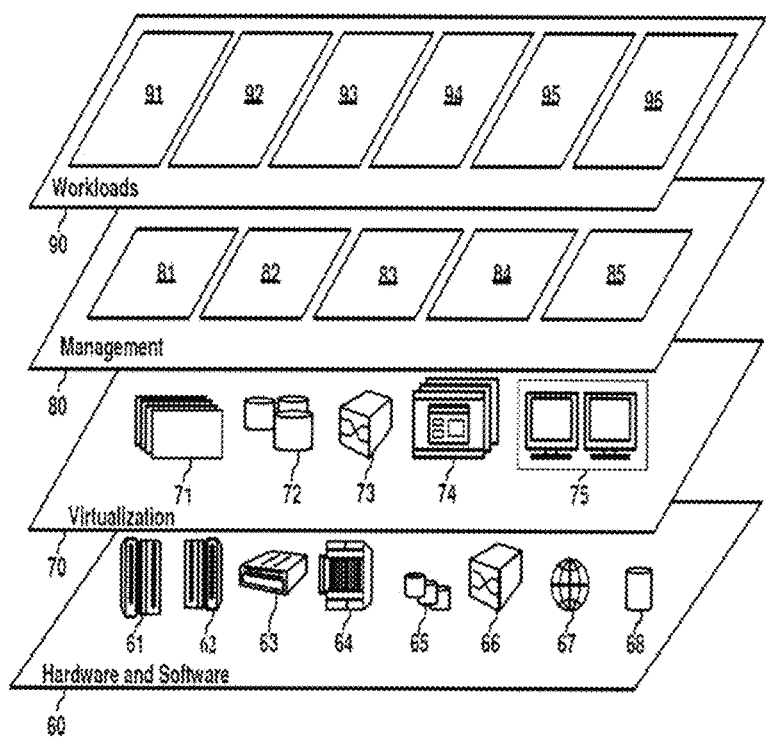
FIG. 7 depicts abstraction model layers, in accordance with embodiments of the present invention.

Referring now to FIG. 7, a set of functional abstraction layers provided by cloud computing environment 50 (see FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and API management or the like 96.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein

What is claimed is:

1. A computer-implemented method for automated gift determination and delivery, comprising:
   receiving, by a processor of a computer system, a contact from an electronic contact list for receiving a gift;
   receiving, by the processor, from first data related to the contact a change in an emotional state of the contact from a previous emotional state to a current emotional state;
   calculating by the processor a confidence level of a reason for the change in the emotional state of the contact, including executing an artificial intelligence computer to train the computer system to identify a plurality of gifts based on the emotional state and previous events involving the contact, comprising:
      determining by the computer system whether to store at least the first data to train the artificial intelligence computer for generating future decisions regarding the contact;
      performing an iteration process to modify a result calculated by the artificial intelligence computer; and
      training, updating, and optimizing the artificial intelligence computer by the processing the result;
      identifying relevant gifts of the plurality of gifts based on the emotional state and previous events involving the contact using the artificial intelligence computer;
   validating, by the processor, from second data the change in the emotional state of the contact;
   receiving, by the processor, third data from a data repository that includes information about the contact to identify the gift based on the information about the contact;
   automatically selecting, by the processor, the gift from the plurality of identified gifts that is determined to be commensurate with the change in the emotional state to the current emotional state of the contact and further commensurate with the information about the contact; and
   displaying, at a computer display of a user purchasing the gift for the contact, in about the gift automatically selected by the processor and an electronic request to approve the selected gift for purchase and delivery to the contact.

2. The method of claim 1, wherein the confidence level is determined from collected social media posts or other published information regarding the emotional state of the contact.

3. The method of claim 1, further comprising:
delivering the gift to the selected contact; and
generating a message regarding the gift, the content of the message determined by the confidence level.

4. The method of claim 3, wherein a first content of the message is generated in response to a first confidence level value and a second content of the message is generated in response to a second confidence level value different than the first confidence level value.

5. The method of claim 1, wherein the first data includes information that is accessible via a network regarding the selected contact, and the second data includes by comparison data between current information of the information accessible via the network and historical information.

6. The method of claim 1, further comprising: generating by the processor a correlation between a plurality of contacts in the electronic contact list and a plurality of specific gifts identified as candidates for providing to the contacts.

7. The method of claim 1, further comprising:
storing emotional state data related to the emotional state of the contact in a data repository;
retrieving the emotional state data from the data repository to determine a subsequent confidence level or subsequent change in an emotional state of the contact; and
electronically training the artificial intelligence computer using the computer system to generate a future decision on a gift determination for the contact.

8. The method of claim 1, further comprising:
determining a recommended gift in response to a determination of the change in emotional state.

9. The method of claim 1, further comprising:
processing data regarding a context of the emotional state; and
further automatically selecting by the processor the gift in response to the processed data regarding the context of the emotional state.

10. A computer system, comprising:
a processor;
a memory device coupled to the processor;
one or more remote computer servers in communication with the processor; and
a computer readable storage device coupled to the processor, wherein the storage device contains program code executable by the processor via the memory device to implement a method for automated gift determination and delivery, comprising:
receiving, by the processor, a contact from an electronic contact list for receiving a gift;
receiving, by the processor, from first data related to the contact a change in an emotional state of the contact from a previous emotional state to a current emotional state;
calculating by the processor a confidence level of a reason for the change in the emotional state of the contact, including executing an artificial intelligence computer to train the computer system to identify a plurality of gifts based on the emotional state and previous events involving the contact, including:
determining by the computer system whether to store at least the first data to train the artificial intelligence computer for generating future decisions regarding the contact;
performing an iteration process to modify a result calculated by the artificial intelligence, computer; and
training, updating, and optimizing the artificial intelligence computer by the processing the result;
identifying relevant gifts of the plurality of gifts based on the emotional state and previous events involving the contact using the artificial intelligence computer;
validating, by the processor, from second data the change in the emotional state of the contact;
receiving, by the processor, third data from a data repository that includes information about the contact to identify the gift based on the information about the contact;
automatically selecting, by the processor, the gift from the plurality of identified gifts that is determined to be commensurate with the change in the emotional state to the current emotional state of the contact and further commensurate with the information about the contact; and
displaying, at a computer display of a user purchasing the gift for the contact, information about the gift automatically selected by the processor and an electronic request to approve the selected gift for purchase and delivery to the contact.

11. The computer system of claim 10, wherein the confidence level is determined from collected social media posts or other published information regarding the emotional state of the contact.

12. The computer system of claim 10, further comprising:
delivering, by the processor, the gift to the selected contact; and
generating, by the processor, a message regarding the gift, the content of the message determined by the confidence level.

13. The computer system of claim 10, wherein the first data includes information that is accessible via a network regarding the selected contact, and the second data includes by comparison data between current information of the information accessible via the network and historical information.

14. The computer system of claim 10, further comprising: generating by the processor a correlation between a plurality of contacts in the electronic contact list and a plurality of specific gifts identified as candidates for providing to the contacts.

15. The computer system of claim 10, further comprising:
storing emotional state data related to the emotional state of the contact in a data repository; and
retrieving the emotional state data from the data repository to determine a subsequent confidence level or subsequent change in an emotional state of the contact; and
electronically training the artificial intelligence computer using the computer system to generate a future decision on a gift determination for the contact.

16. The computer system of claim 10, further comprising:
determining a recommended gift in response to a determination of the change in emotional state.

17. The computer system of claim 10, further comprising:
processing data regarding a context of the emotional state; and
further automatically selecting by the processor the gift in response to the processed data regarding the context of the emotional state.

18. A computer program product, comprising a computer readable hardware storage device storing a computer readable program code, the computer readable program code comprising an algorithm that when executed by a computer processor of a computer system implements a method for automated gift determination and delivery, comprising:

receiving, by a processor of a computer system, a contact from an electronic contact list for receiving a gift;

receiving, by the processor, from first data related to the contact a change in an emotional state of the contact from a previous emotional state to a current emotional state;

calculating by the processor a confidence level of a reason for the change in the emotional state of the contact, including executing an artificial intelligence computer to train the computer system to identify a plurality of gifts based on the emotional state and previous events involving the contact, including:

determining by the computer system whether to store at least the first data to train the artificial intelligence computer for generating future decisions regarding the contact;

performing an iteration process to modify a result calculated by the artificial intelligence computer; and training, updating, and optimizing the artificial intelligence computer by the processing the result;

identifying relevant gifts of the plurality of gifts based on the emotional state and previous events involving the contact using the artificial intelligence computer;

validating, by the processor, from second data the change in the emotional state of the contact;

receiving, by the processor, third data from a data repository that includes information about the contact to identify the gift based on the information about the contact;

automatically selecting, by the processor, the gift from the plurality of identified gifts that is determined to he commensurate with the change in the emotional state to the current emotional state of the contact and further commensurate with the information about the contact; and displaying, at a computer display of a user purchasing the gift for the contact, information about the gift automatically selected by the processor and an electronic request to approve the selected gift for purchase and delivery to the contact.

* * * * *